(12) United States Patent
Pando

(10) Patent No.: US 8,151,373 B2  
(45) Date of Patent: Apr. 10, 2012

(54) GLOVE WITH INSECT PROOFING

(76) Inventor: Brenda Pando, Corona, CA (US)

( * ) Notice: Subject to any disclaimer, the term of this patent is extended or adjusted under 35 U.S.C. 154(b) by 1901 days.

(21) Appl. No.: 10/970,063

(22) Filed: Oct. 20, 2004

(65) Prior Publication Data

US 2007/0067890 A1    Mar. 29, 2007

(51) Int. Cl.  
*A41D 19/00* (2006.01)

(52) U.S. Cl. .............................. 2/161.6; 2/162

(58) Field of Classification Search .......... 2/16, 20, 2/161.1, 160, 162, 170; 15/227; 383/64  
See application file for complete search history.

(56) References Cited

U.S. PATENT DOCUMENTS

| | | | | |
|---|---|---|---|---|
| 4,523,586 A * | 6/1985 | Couri | ................................. | 602/3 |
| 4,868,927 A * | 9/1989 | Bourdeau et al. | .............. | 2/161.1 |
| 4,884,300 A * | 12/1989 | Vistins | ............................... | 2/162 |
| 5,063,919 A * | 11/1991 | Silverberg | ........................ | 602/3 |
| 5,381,557 A * | 1/1995 | Luria et al. | ........................... | 2/16 |
| 5,673,435 A | 10/1997 | Gebhard | | |
| 5,704,670 A * | 1/1998 | Surplus | ............................ | 294/25 |
| 6,203,080 B1 * | 3/2001 | Surplus | .......................... | 294/1.3 |
| 6,237,971 B1 * | 5/2001 | Ward Gilley | ................... | 294/1.3 |
| 6,393,614 B1 * | 5/2002 | Eichelbaum | ....................... | 2/160 |
| 6,402,375 B1 * | 6/2002 | Schreiter et al. | ................ | 383/64 |
| 6,511,111 B2 * | 1/2003 | Dooley | ........................... | 294/1.3 |
| 6,516,469 B1 | 2/2003 | Schaetzel | | |
| 6,539,549 B1 * | 4/2003 | Peters, Jr. | ............................ | 2/16 |
| 6,748,603 B1 * | 6/2004 | Schmitt et al. | ..................... | 2/159 |

* cited by examiner

*Primary Examiner* — Katherine Moran  
(74) *Attorney, Agent, or Firm* — Fish & Associates, PC

(57) ABSTRACT

The inventive subject matter is directed toward a glove having a hand receiving opening and a sealing mechanism that substantially seals the hand receiving opening.

8 Claims, 1 Drawing Sheet

GLOVE WITH INSECT PROOFING

FIELD OF THE INVENTION

The field of the invention is gloves.

BACKGROUND OF THE INVENTION

It is common for insects, arachnids, and other pests to crawl into gloves, shoes, and other clothing articles. This is especially prevalent with gloves because the finger areas provide a small dark space that pests find a suitable place in which to live.

In order to avoid coming into contact with a pest, people generally shake out or at least visually examine their gloves or other articles of clothing. Because pests can lodge themselves deep into the finger areas of a glove, shaking and visually inspecting may prove to be inadequate. Sometimes people will stomp on or otherwise try to press on the outside of the glove in order to find out whether a pest is inside. For some pests, this may work but for others, it is also inadequate especially if the pest locates itself in an area that is resistant to stomping.

Of course, one could enclose his gloves in a sealable plastic bag, suitcase, or other sealable storage item, but this is time consuming and moreover the item is likely to be hidden from view by the storage item.

Thus, there is a need for new devices and methods directed toward preventing pest infestation into gloves.

SUMMARY OF THE INVENTION

The present invention provides a glove having a hand receiving opening and a sealing mechanism that substantially seals the hand receiving opening.

Various objects, features, aspects and advantages of the present invention will become more apparent from the following detailed description of preferred embodiments of the invention, along with the accompanying drawings in which like numerals represent like components.

BREIF DESCRIPTION OF THE DRAWING

DETAILED DESCRIPTION

Figure 1:
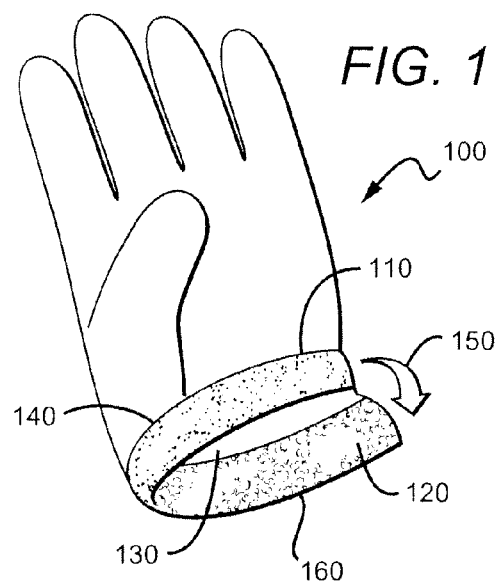
FIG. 1 is a schematic of a glove with a sealing mechanism comprised of hook and loop material.

Referring first to FIG. 1, a glove 100 has an inner collar made up of an upper portion 140 and a lower portion 160. The upper portion comprises a strip of hook material 110 and the lower portion comprises a strip of loop material 120 (e.g. Velcro™). In order to show both the hook and loop materials, the glove is shown with the upper portion 140 of the inner collar area folded out. Arrow 150 shows the direction in which the upper portion 140 will be moved toward the lower portion 160 when the glove is in its normal configuration. Note that a defined "collar area" is not a requirement of the inventive subject matter and that "collar" is used to refer to the portion of the glove furthest away from the tips of the fingers.

Here, a sealing mechanism is comprised of a strip of hook material 110 and a strip of loop material 120 arranged on the inner surface of the hand receiving area 130. It will be recognized by one of skill in the art that hook and loop material is the generic name for the commonly used trademark Velcro™. An inherent characteristic of this type of sealing mechanism is that it can be substantially sealed and re-sealed numerous times without replacing any of the constituent materials. "Substantially seals" means sealing that is sufficient to prevent entry of most insects, arachnids, and other common pests. More specifically, the sealing mechanism prevents entry of pests to the extent that the sealing mechanisms proposed herein are capable. It should be understood that some sealing mechanisms will seal more completely than others, but the overall inventive concept includes all sealing mechanisms that can prevent entry of a typical household size spider, scorpion, and cockroach. In addition to Velcro™, a sealing mechanism may additionally or alternatively include a zipper, a zip seal, and a reinforced fold. Some gloves may utilize more than one sealing mechanism. For purposes of comparison, gloves that utilize elastic or draw string around the hand entry portion are not considered to have a sealing mechanism because they do not substantially seal the hand receiving opening.

Figure 2:
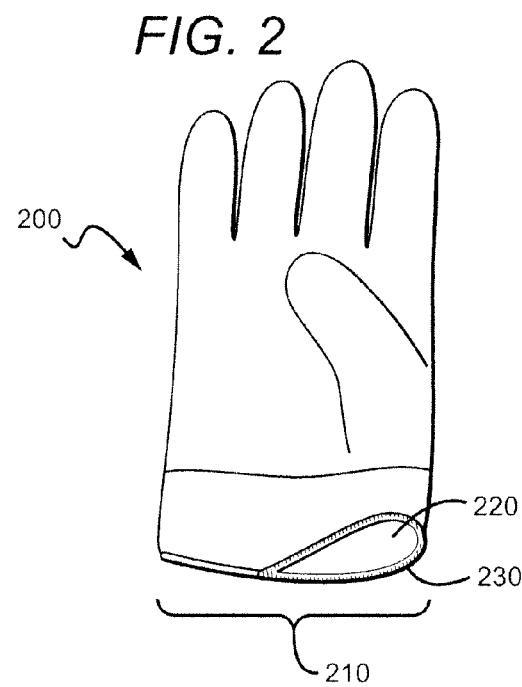
FIG. 2 is a schematic of an alternative glove with a sealing mechanism comprised of a zipper.

FIG. 2 depicts a glove 200 having a zipper 210. The zipper 210 shown here is partially zipped (i.e. partially sealed) and therefore a portion of the hand receiving area 220 and the unzipped teeth 230 can be observed.

It is generally contemplated that the hand receiving area has an unsealed diameter of approximately 10 cm although other diameters may be appropriate so long as a hand can fit through the opening when the sealing mechanism is completely unsealed.

Figure 3:
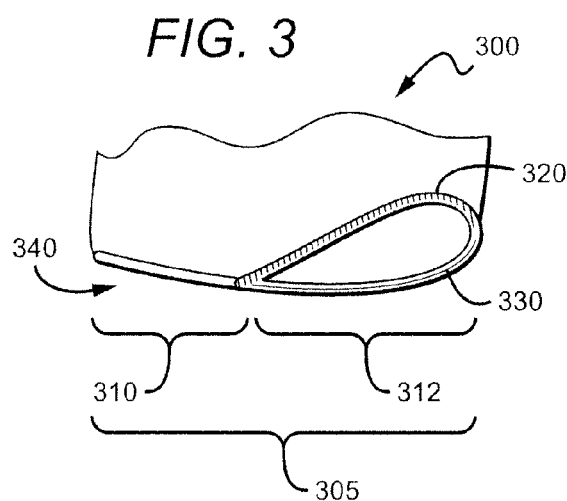
FIG. 3 is a schematic of a portion of an alternative glove with a sealing mechanism comprised of a zip seal.

FIG. 3 shows a collar area 300 of a glove that has a zip seal 305 type sealing mechanism. A zip seal by itself is known in the field that includes sandwich bags; however, to the inventor's knowledge such a sealing mechanism has never been used for the applications described herein. The zip seal 305 in FIG. 3 is shown partially sealed and therefore has a sealed portion 310 and an unsealed portion 312. The zip seal 305 works by compressing an opposing lip 320 into a groove 330.

While zip seal 305 is located at the bottom most portion of the collar area (identified by numeral 340), it is contemplated that the zip seal 305 can be located along the inside portion of collar. If the zip seal is located along the inside surface of the collar (i.e. that surface closest to the wearer's hand), it is preferable for the zip seal to be located relatively close to the bottom 340 of the collar area so that there is relatively little inside area left unsealed.

Figure 4:
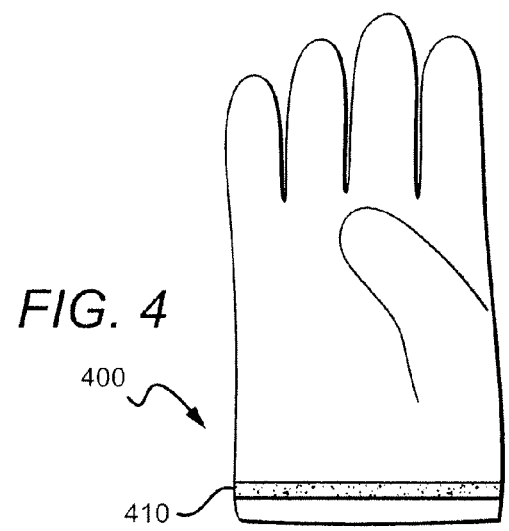
FIG. 4 is a schematic of a glove having a sealing mechanism on the outside surface of the glove.

FIG. 4 shows a glove 400 having hook and loop material 410 mounted on the outside of the glove. In this embodiment of the inventive subject matter, the glove is designed as to be sealed inside out to preserve forensic matter that may have been collected on the outside of the glove. This embodiment contemplates that the glove can be used for forensics or other activities that require preservation of evidence. Another application includes sealing hazardous material onto a glove and in this respect it is contemplated that sealable gloves may be worn by surgeons and other doctors.

Functionally, the glove 400 is removed from the users hand by pulling the outside of the glove over the inside thereby leaving the glove in a substantially inside out state. The glove is then sealed and the forensic evidence or other material on the outside of the glove is preserved. In this case, it is not necessary that the sealing mechanism be resealable and therefore other types of sealing mechanisms are contemplated including, most especially, those that have a strip of adhesive that is revealed by peeling back a protective cover.

Thus, specific embodiments and applications of a sealable glove have been disclosed. It should be apparent, however, to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

What is claimed is:

1. A glove having:
   a hand receiving opening at an end of the glove that leads to a hand-receiving cavity with mutually facing first and second inner surfaces; and
   a sealing mechanism that substantially seals the hand receiving opening while the glove is disposed in a configuration such that the inner surfaces are still facing one another, and while the hand is not disposed within the glove.

2. The glove of claim 1, wherein the hand receiving opening has an unsealed diameter of at least 7 cm.

3. The glove of claim 1, wherein the sealing mechanism comprises a zipper.

4. The glove of claim 1, wherein the sealing mechanism comprises hook and loop material.

5. The glove of claim 1, wherein the sealing mechanism comprises a zip seal.

6. The glove of claim 1, wherein the sealing mechanism is disposed along an inside surface of the glove.

7. The glove of claim 1, wherein the sealing mechanism is disposed along an inner surface of the glove.

8. A glove for receiving a hand, comprising:
   a collar area through which the hand can be inserted;
   a body cavity that receives the hand; and
   first and second areas on opposing inner sides of the collar area, which mate to seal the cavity sufficiently to prevent entry of insects into the body while the hand is not disposed within the glove.

* * * * *